United States Patent [19]

Akkara et al.

[11] Patent Number: 5,981,240
[45] Date of Patent: Nov. 9, 1999

[54] ENZYME-CATALYZED SYNTHESIS OF MACROMOLECULES IN ORGANIC SOLVENTS

[75] Inventors: Joseph A. Akkara, Holliston; Ferdinando F. Bruno, Andover, both of Mass.

[73] Assignee: The United States of America as represented by the Secretary of the Army, Washington, D.C.

[21] Appl. No.: 09/173,607

[22] Filed: Oct. 2, 1998

Related U.S. Application Data

[63] Continuation-in-part of application No. 08/774,329, Nov. 27, 1996.
[51] Int. Cl.[6] .................................. C12P 7/62; C12N 9/50
[52] U.S. Cl. ..................... 435/135; 435/174; 435/177; 435/213; 435/219; 435/221; 435/222
[58] Field of Search ...................... 435/135, 177, 435/174, 213, 219, 221, 222

[56] References Cited

U.S. PATENT DOCUMENTS 5,719,039  2/1998  Dordick et al. .......................... 435/213

OTHER PUBLICATIONS

Derwent Computer Biotechds 93–01794 Rao Et Al "The Use Of Pressure To Modify Enzyme Activity In Reversed Micelles; Prssurization Of Lipase And Chymotrypsin–Containing Aot–Water Isooctane Reversed Micelle May Be Used As A Switch For Lipase Reactions" Biot, 1992.

Derwent Computer Biotechnds 94–04152 Paradkar Et Al "Mechanism Of Extraction Of Chymotrypsin Into Isooctane At Very Low Concentrations Of Aerosol Ot In The Absence Of Reversed Micelles. . " Biotechnol Bioeng. (1994) 43, 6, 529–540, 1994.

*Primary Examiner*—Herbert J. Lilling
*Attorney, Agent, or Firm*—Vincent J. Ranucci

[57] ABSTRACT

A method is described for a simple, fast and efficient synthesis of homopolymers and copolymers by the enzymatic ring opening polymerization of lactones and lactides. The enzyme used is an ion paired protease. The advantage of this enzymatic system is in using small amount of enzyme per monomer and lower reaction time. Homopolymers and copolymers are synthesized with molecular weights between 1000 and 4600 daltons, and dispersity as low as 1.1. The monomer conversion after 4 days, for reactions catalyzed by protease S, has reached 100%. Different initiators are used to control the rate and degree of polymerization. Synthesis of block copolymers with defined block size and crystallinity are described in this invention. These biodegradable and bioerodable polyesters and copolyesters with controlled molecular weight, dispersity and crystallinity have applications in medical, drug, cosmetic and food industries.

40 Claims, 7 Drawing Sheets

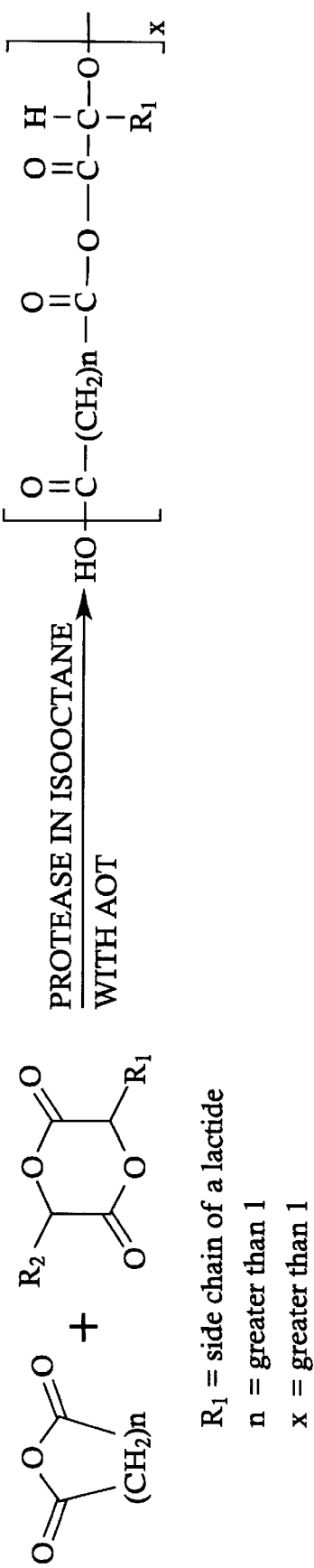
Figure 1 Schematics of a copolyester synthesis from a lactone and a lactide by a protease-catalyzed reaction in isooctane with AOT

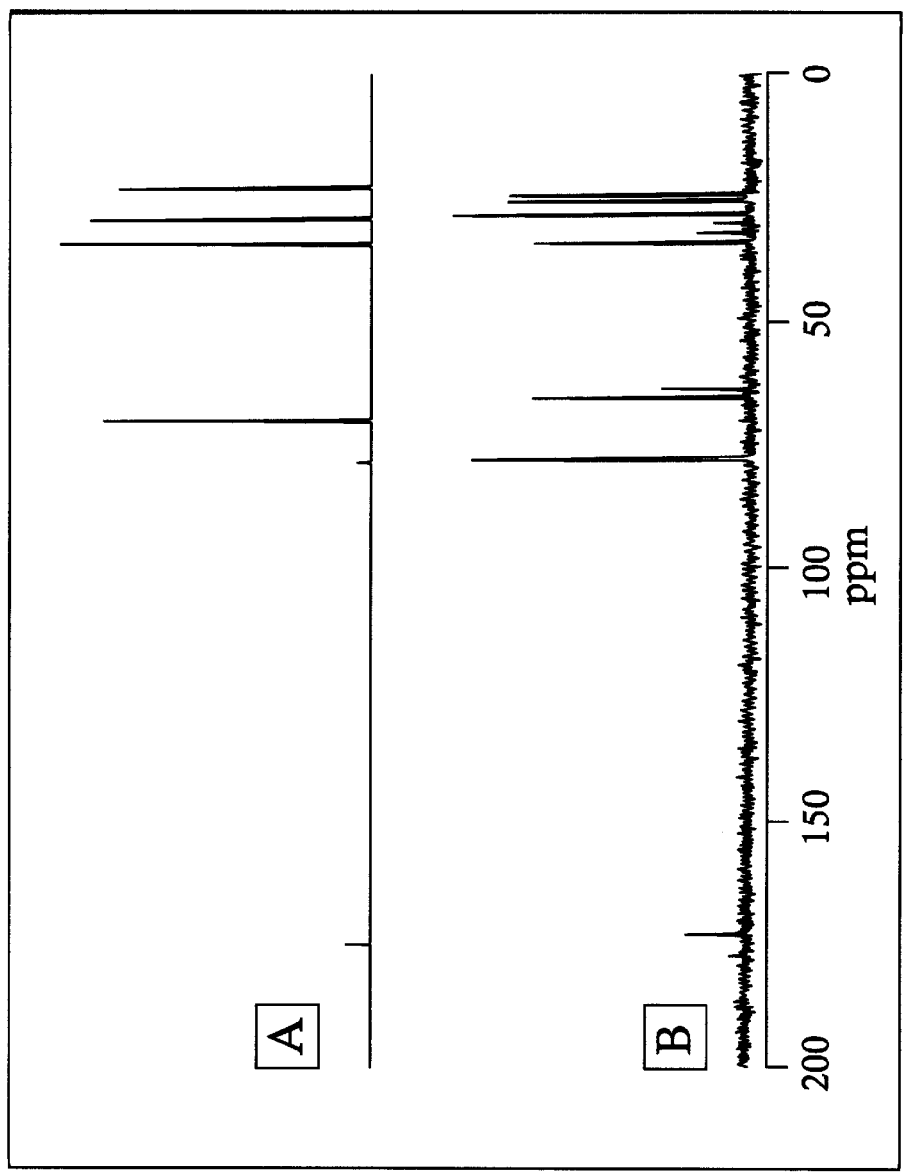
Figure 2 $^{13}$C NMR of ε-caprolactone (monomer sample A), and poly(ε-caprolactone) (polymer sample B).

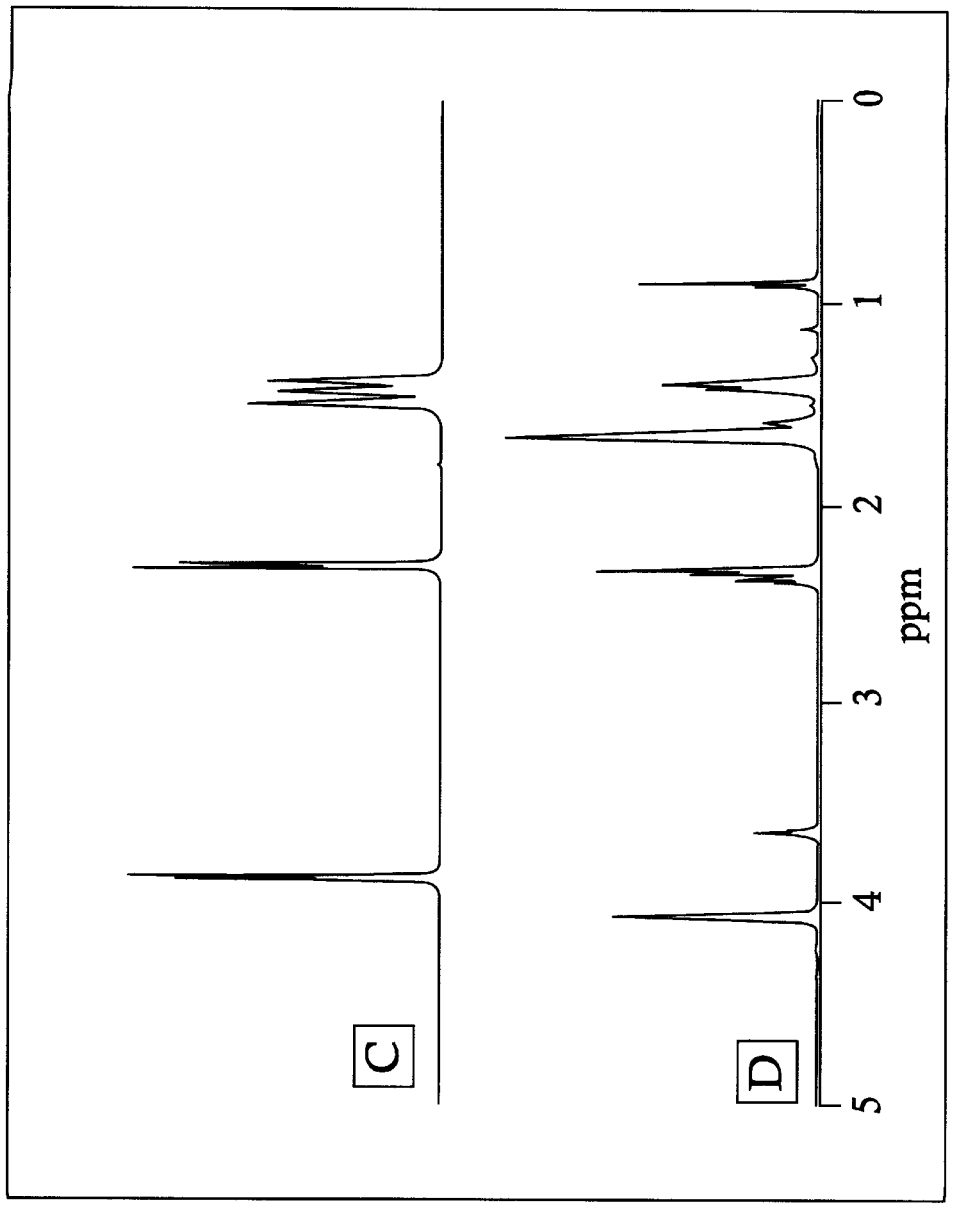
Figure 3 $^1$H NMR of ε-caprolactone (monomer sample C), and poly(ε-caprolactone) (polymer sample D).

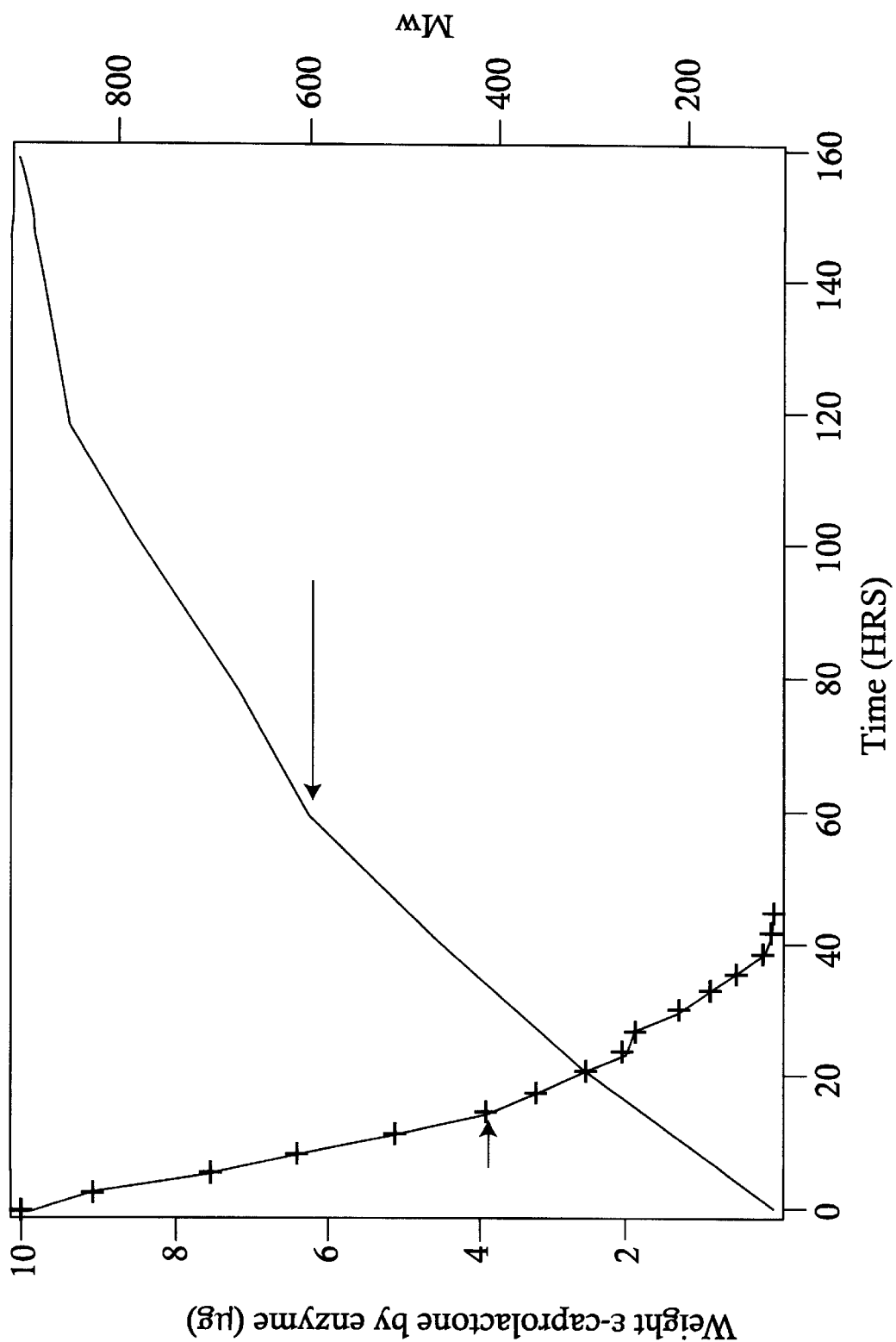
Figure 4 Kinetics of ring opening polymerization of ε-caprolactone by enzyme catalysis

| Monomer | Initiator | Enzyme | Rx time (days) | Rx time (GPC) | Dispersity (Mw/Mn) | Mol. Wt. (¹H NMR) | Conv. (%) |
|---|---|---|---|---|---|---|---|
| ε-Caprolactone | Butanol | Protease N | 7 | 4605 | 1.14 | 4320 | 100.0 |
| " | Water | " | 7 | 3110 | 1.40 | 3080 | 100.0 |
| " | None | " | 7 | 943 | 1.90 | 1070 | 100.0 |
| δ-Valerolactone | " | " | 7 | 1590 | 1.52 | 1498 | 82.2 |
| Dilactone # | " | " | 7 | 1285 | 1.05 | 1125 | 48.3 |
| ε-Caprolactone | " | Protease S | 4 | 2571 | 1.43 | 2490 | 100.0 |
| δ-Valerolactone | " | " | 4 | 3267 | 1.52 | 3110 | 100.0 |
| Dilactone # | " | " | 4 | 1435 | 1.15 | 1240 | 100.0 |

Figure 5. Properties of polyesters synthesized from different monomers with different initiators and Proteases

| Monomer | Feed | Mol. Wt. ($^1$H NMR) | Tc (days) | Tm (GPC) | Tg (Mw/Mn) |
|---|---|---|---|---|---|
| δ-Valerolactone/ ε-Caprolactone | 1:3 | 3306 | 15.6 | 30.2 | nd |
| " | 2:2 | 4227 | 21.9 | 34.9 | nd |
| " | 3:1 | 2275 | 16.7 | 38.7 | nd |
| δ-Valerolactone/ Dilactone # | 3:1 | 612 | -21.6 | 16.7 | -19.5 |
| " | 2:2 | 1512 | nd | nd | nd |
| " | 3:1 | 636 | -23.9 | 16.5 | -19.5 |
| ε-Caprolactone/ Dilactone # | 3:1 | 1477 | nd | 26.6 | -2.2 |
| " | 2:2 | 1515 | nd | nd | nd |

(3S)-cis-3,6-Dimethyl-1,4-dioxane-2,5-dione

Figure 6. Thermal properties of copolyesters prepared from δ-valerolactone, ε-caprolactone, and dilactone

| Monomer | Feed | Enzyme | Rx time (days) | Mol. Wt. (Mw) | Mol. Wt. (Mn) | Dispersity (Mw/Mn) |
|---|---|---|---|---|---|---|
| δ-Valerolactone/ ε-Caprolactone | 1:3 | Protease N | 7 | 3306 | 1545 | 1.14 |
| " | 2:2 | " | 7 | 4227 | 1430 | 2.19 |
| " | 3:1 | " | 7 | 2275 | 944 | 2.41 |
| δ-Valerolactone/ Dilactone # | 3:1 | " | 7 | 612 | 437 | 1.40 |
| " | 2:2 | " | 7 | 1512 | 963 | 1.57 |
| " | 3:1 | " | 7 | 636 | 501 | 1.27 |
| ε-Caprolactone/ Dilactone # | 3:1 | " | 7 | 1477 | 717 | 2.06 |
| " | 2:2 | " | 7 | 1515 | 557 | 2.72 |
| " | 1:3 | " | 7 | 865 | 636 | 1.36 |

(3S)-cis-3,6-Dimethyl-1,4-dioxane-2,5-dione

Figure 7. Molecular weight [both Weight average (Mw) and Number average)] and dispersity of copolyesters synthesized by Protease N catalyzed reactions.

ENZYME-CATALYZED SYNTHESIS OF MACROMOLECULES IN ORGANIC SOLVENTS

CROSS-REFERENCE TO RELATED APPLICATION

This application is a continuation-in-part of U.S. patent application Ser. No. 08/774,329, filed Nov. 27, 1996, in the name of Joseph A. Akkara et al.

STATEMENT OF GOVERNMENT INTERESTS

The invention described herein may be manufactured and used by the Government for government purposes without the payment of any royalty thereon.

FIELD OF INVENTION

The present invention relates to the enzyme-catalyzed synthesis of homopolyesters and copolyesters from lactones and lactides in organic solvents.

BACKGROUND OF THE INVENTION

Selective synthesis of macromolecules is desirable to tailor their structural and functional properties, such as hydrophobicity, hydrophilicity, and interfacial and film forming properties. E.g., polyesters synthesized by enzymes may be useful as time-release bioerodable and biodegradable drug delivery matrices such as coatings, finishes and films, and biodegradable emulsifiers, compatibilizers and detergents.[1] However, selective synthesis of polyesters by chemical reactions are difficult due to multiple steps involved in the modification (protection, deprotection, extraction, separation and purification), and due to the difficulty in controlling molecular weight and polydispersity and hence lack of specificity and solubility of the polymer.[2] Moreover, some of the polyesters synthesized by chemical methods are neither biodegradable nor bioerodable.

Enzymes are powerful catalysts in organic solvents where they catalyze a wide variety of reactions that are difficult to perform in aqueous media. This is particularly evident in esterification reactions catalyzed by lipases and proteases wherein a variety of nucleophiles act as substrates for enzyme-catalyzed acyl transfer in nearly anhydrous organic solvents. The development of suitable techniques for the synthesis of polyesters and copolyesters in organic solvents, therefore, would represent both an opportunity for the synthesis of novel materials as well as means to overcome a technical hurdle in the broader uses of enzymes in non-aqueous media.

Polyesters synthesized by enzymes are of great interest for their mechanical properties, biodegradability, bioerodability and applications in drug delivery systems.[3] Recent investigations have shown that lactones can be polymerized in presence of enzymes such as lipases.[4–7] However, the following serious drawbacks of this technique were reported in the reaction procedures: high concentrations of enzyme in the system; long reaction time required for the polymerization to reach completeness; and one time use of enzyme. Such limitations were prohibitive for an industrial application using the enzymatic path.

Proteases are enzymes capable to catalyze peptide and ester bond synthesis in various organic solvents.[8–9] Here we propose a novel approach using low amounts of protease enzyme in an non-aqueous solution to catalyze the polymerization and copolymerization of lactones and lactides in presence of different initiators. In addition, this protease mediated polymerization in solution produces polyesters and copolyesters with defined molecular weight and dispersity. A method is also described for the synthesis of copolyesters, wherein the composition of the copolymer is predetermined by the initial monomer composition of the lactones and lactides. A method to achieve enzyme solubilization in organic solvents through formation of hydrophobic ion-pairs between an enzyme and a charged surfactant was previously used.[10] In particular, it has been observed that subtilisin Carlsberg (from *Bacillus licheniformis*), protease N (*Bacillus subtilis*), and protease S (*Bacillus specific*) ion paired with the anionic surfactant dioctylsulfosuccinate, sodium salt (aerosol OT or AOT), remained predominantly active in isooctane.[11, 12] In addition, these microbial protease are commercially available and is much cheaper than lipases.

This system, containing proteases ion paired with a detergent, was successfully used for the regioselective acylation of sugars[12] and of polysaccharides with alkyl vinyl esters.[13] The ion-pairing in organic solvents of protease enzymes is a valuable tool toward the catalysis of other reactions that implement a polyesterification of a substrate with specific initiators.

Accordingly, it is an object of this invention to overcome the above illustrated inadequacies and problems of enzyme-based polyester synthesis by providing an improved method.

It is the object of this invention to use ion paired protease enzymes in organic solvents for the synthesis of polyesters from different lactones and lactides in reasonable times for industrial applications.

It is another object of this invention to provide a method of synthesizing homopolyesters and copolyesters from lactones and lactides wherein their selective polymerization results in structural and/or functional benefits.

It is object of this invention to provide a method of synthesizing polyesters and copolyesters from lactones and lactides wherein the polymers synthesized are of selective and predictable molecular weight with well defined molecular weight and narrow molecular weight-dispersity and resultant structural and/or functional benefits. Polymers with such well defined molecular weight and dispersity are required for drug and cosmetic preparations or systems for time defined release, breakdown and/or biodegradation both in vivo and in vitro.

It is another object of this invention to provide a method of synthesizing copolyesters from lactones and lactides wherein the copolymers synthesized are of decreased crystallinity and increased processability.

It is another object of the present invention to provide a method of enabling the use of enzymes to catalyze reactions in non-aqueous media for the synthesis of biodegradable, bioerodable and biocompatible polymers.

It is another object of this invention to provide a method of enabling the use of proteases to synthesize polyesters and copolyesters from lactones and lactides, wherein the proteases are commercially available and are much cheaper than lipases.

Yet it is another object of the present invention to provide a method of enabling the use of enzymes to catalyze polymerization reactions in non-aqueous media, wherein the enzyme and the reaction media can be reused and/or recycled for subsequent polymerization reactions.

SUMMARY OF THE INVENTION

The present invention provides processes for the enzyme-based production of homopolyesters and copolyesters from lactones and lactides in non-aqueous media, wherein the polymers synthesized are of well defined molecular weight and narrow molecular weight dispersity. Such attributes are novel because chemical synthetic methods are unable to make polyesters and copolyesters with well defined molecular weight and narrow molecular weight-dispersity for biodegradable and bioerodable applications. The processes also emphasize the use of mild reaction conditions such as temperature, pressure and pH, recycling or reuse of the reaction media leading to waste minimization, minimal by product formation, and minimal separations and purifications. Reaction media and the catalysts can be easily regenerated to minimize product cost and environmental hazard.

Recently, a method was developed to solubilize enzymes in hydrophobic organic solvents through the formation of enzyme-surfactant ion pairs.[10] These ion-paired, organic-soluble enzymes are extremely active in hydrophobic solvents, such as isooctane. The present invention demonstrates the synthesis of homopolyesters and copolyesters from lactones and lactides in organic solvents using an organic-soluble enzyme preparation of subtilisin (from *Bacillus subtilis*). This represents the first attempt at catalyzing the synthesis of biodegradable and bioerodable homopolyesters and copolyester using proteases in organic solvents.

According to one aspect of the present invention, there is disclosed a method for the synthesis of homopolyester or copolyester compounds by polymerizing one or more lactones, at least one of said one or more lactone monomers having the following structure:

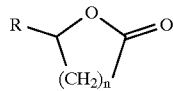

wherein
R is hydrogen, alkyl, alkenyl, alkoxyl, cycloalkyl, cycloalkoxyl or alkylaryl group having from 0 to about 20 carbon atoms, or alkyl group having from 1 to about 20 carbon atoms substituted with carboxylic acid or sulfonic acid substituents;
n is an integer equal to or greater than 1;
Preferred for use in the practice of this invention are lactones of the above formula in which:
R is a hydrogen, methyl, ethyl, propyl, butyl or pentyl group;
n is an integer from 1 to 6;
Particularly preferred embodiments for use in the practice of this invention for the polymerization of lactones of the above formula in which;
R is a hydrogen, methyl or ethyl group
n is an integer from 1 to 3;
According to another aspect of the present invention, there is disclosed a method for the synthesis of polyester or copolyester compounds by polymerizing one or more lactides, at least one of said one or more lactide monomers having the following structure:

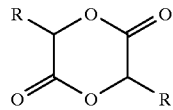

wherein
R is hydrogen, alkyl, alkenyl, alkoxyl, cycloalkyl, cycloalkoxyl or alkylaryl group having from 0 to about 20 carbon atoms, or an alkyl having from 1 to about 20 carbon atoms substituted with carboxylic acid or sulfonic acid substituents;
Preferred for use in the practice of this invention are lactides of the above formula in which:
R is a hydrogen, methyl, ethyl, propyl butyl or pentyl group;
Particularly preferred embodiments for use in the practice of this invention for the polymerization of lactides of the above formula in which;
R is a methyl or ethyl group According to one aspect of the present invention, there is disclosed a copolyester compound synthesis by polymerizing one or more lactones and lactides, at least one of said one or more lactone and lactide monomers having structures described above.

Another aspect of this invention is the use initiators for the polymerization of lactones and lactides. Initiators for the polymerization of lactones and lactides are selected from a group of compounds with hydroxyl groups. In addition, these compounds with hydroxyl groups are selected from a class of compounds for their ability, when present in the reaction media, to produce polymers with well defined and defined molecular weight and dispersity. Examples of compounds with hydroxyl groups used for the polymerization of various lactones and lactides are water, butanol, α-cyclodextrins, β-cyclodextrins, γ-cyclodextrins, amylose, hyaluronic acid, chitosan and starch.

One benefit associated with the present invention is the use ion paired protease enzymes in organic solvents for the synthesis of polyesters from different lactones and lactides in reasonable times for industrial applications. Of particular importance for industrial applications is the use of proteases to synthesize polyesters and copolyesters from lactones and lactides, wherein the proteases are commercially available and are much cheaper than lipases. In addition, the present invention describes a method of enabling the use of enzymes to catalyze polymerization reactions in non-aqueous media, wherein the enzyme and reaction media can be reused for subsequent polymerization reactions. Structural and functional properties of polyesters synthesized by enzyme-catalyzed reactions can be controlled by the preselection of monomers lactones and lactides. The pre-selection of the monomers for the polymer synthesis can also be used to control the crystallinity and processability of polyester synthesized. Polyesters synthesized by enzyme-catalyzed reactions are biodegradable, bioerodable and biocompatible polymers, and have applications in drug delivery systems and formulations. In addition, polyesters and copolyesters with well defined molecular weight and dispersity have applications in time release systems in coatings, finishes, fibers, membranes and films. Of particular importance is the potential use of these low cost polyesters for edible coatings, wrapping and films to be utilized for food preservation and storage.

Other objects, features and advantages will be apparent from the following detailed description of preferred embodiments thereof taken in conjunction with the accompanying drawings.

BRIEF DESCRIPTION OF THE DRAWINGS

FIG. 1 Proposed schematics of a copolyester synthesis from a lactone and a lactide by a protease catalyzed reaction in isooctane with AOT.

FIGS. 2A and 2B $^{13}$C NMR of caprolactone (monomer sample A), and polycaprolactone (polymer sample B).

FIGS. 3C and 3D $^{1}$H NMR of caprolactone (monomer sample C), and polycaprolactone (polymer sample D).

FIG. 4 Kinetics of ring opening polymerization of ε-caprolactone by enzyme catalysis.

FIG. 5 Properties of homopolyesters synthesized from different monomers with different initiators and proteases FIG. 6 Thermal properties of copolymers prepared from δ-valerolactone, ε-caprolactone and dilactide.

FIG. 7 Molecular weight [both weight average (Mw) and number average (Mn)] and dispersity of copolyesters synthesized by Protease N catalyzed reactions.

DETAILED DESCRIPTION OF EMBODIMENTS

The enzymatic process described herein can be envisioned as a new method for the selective synthesis of macromolecules such as homopolymers and copolymers of polyesters in nonaqueous media. This approach is amenable to a wide range of enzymes and lactones and lactides. Preparatory to experimental verification of the present invention, *Bacillus subtilis* (1.1 mg/mL, Protease N or Protease S) was dissolved in N-[2-hydroxyethyl]piperazine-N'-[2-ethanesulfonic acid] (HEPES) or 1,3-bis[tris(hydroxymenthyl)-methylamino]propane (BTP) buffer (10 mM, pH 7.8) containing 6 mM KCl. The aqueous solution was mixed with an equal volume of isooctane containing 2 mM dioctysulfosuccinate, sodium salt (AOT) and the biphasic solution at 25° C. was stirred at 250 rpm. After 30 minutes the phases were allowed to separate and the organic phase was removed.[10] The protein and the water content of the isooctane solution were determined by absorbance at 280 nm and Karl-Fischer titration, respectively. Based on the measurements, approximately 1.0 mg/mL of enzyme was in the isooctane solution with a water content of <0.01%. This enzyme solution in isooctane containing AOT was used for the synthesis of macromolecules such as polyesters and copolyesters described below.

EXAMPLE 1

The dry monomers, ε-caprolactone (ECL), (3S)-cis-3,6-Dimethyl-1,4-dioxane-2,5-dione (DILAC), γ-caprolactone (GCL), γ-butyrolactone (GBL), and δ-valerolactone (DVL) (Aldrich Chemical Co. Milwaukee, Wis.) were contacted with the organic solution. The reactions were performed with 1.0 mg/mL enzyme in isooctane containing 440 mM monomer with shaking (200 rpm) at 55° C. for Protease N, and at 70° C. for Protease S respectively. Examples of initiators used to control the rate and degree of polymerization of monomers (lactone and lactide) were butanol, water, the water already present in the ion paired enzyme, α-cyclodextrins, β-cyclodextrins, γ-cyclodextrins, amylose, hyaluronic acid, or starch. Concentration of the initiators used in the polymerization reaction mixture varied from 0.01 mM to 0.3 mM, based on the initiator, the molecular weight and dispersity of the polymer (both homopolymer and copolymer) required, and the type of monomer (lactone and lactide) used for the polymerization. The polymer was removed from the reactor vial and was washed with fresh isooctane to remove unreacted monomers and detergent. The final samples were then dissolved in chloroform and the insoluble part was washed in fresh isooctane three times.

EXAMPLE 2

Control reaction were performed for each experiment. The procedure for the controls were analogous to the enzymatic polymerization, with the difference that enzyme was not utilized in one set of control experiments. In another set of control experiments, a denatured protease was implemented in an additional control. Polymerization with such denatured enzyme was unsuccessful with all monomers.

EXAMPLE 3

Polymerization (also refereed to as bulk polymerization) of all monomers without detergent solubilization of the proteases, was performed on all monomers with the following procedure: 20 ml of monomer (neat) were contacted with 20 mg of protease enzyme. The reaction was conducted at 55° C. or 70° C. for 7 or 4 days under agitation. The final product was separated and analyzed for quantitative measurements. Control experiment were performed with the same procedure but in absence of enzyme. The control and the bulk polymerization did not produce any polymer.

EXAMPLE 4

Examples of other monomers evaluated for polymerization were γ-caprolactone, ∂-hexalactone, ∂-nonalactone, ∂-decalactone, ∂-undecalactone, ∂-dodecalactone, ∂-tetradecalactone, ε-decalactone, ω-6-hexadecalactone, and ω-pentadecalactone (Aldrich Chemical Co.). Various degrees of polymerizations were observed with these monomers. Some examples of monomers selected from a group of lactones and lactides used for polymerization reactions catalyzed by proteases in organic solvents are given in FIGS. 5 to 7.

EXAMPLE 5

Copolymers were prepared from lactones and lactide using the ion-paired enzyme. Examples of three such systems [ε-caprolactone (ECL), δ-valerolactone (DVL) and dilactide (DILAC)] are given here. As an example of first system was formed by monomers ECL and DVL, the second by DVL and DILAC and the third one by ECL and DILAC (all initial feed compositions for each system were of 3:1, 2:2 and 1:3 molar ratio).

EXAMPLE 6

The polymers and copolymers were analyzed using proton ($^1$H) Nuclear Magnetic Resonance ($^1$H NMR), Carbon ($^{13}$C) Nuclear Magnetic Resonance ($^{13}$C NMR), Differential Scanning Calorimetry (DSC), Thermal Gravimetric Analysis (TGA), Gel Permeation Chromatography (GPC), Fourier Transform Infrared (FTIR) and cross polarized optical microscope. Quantitative analysis of the different triads were evaluated using $^{13}$C NMR according previous procedure.[14] The assignment for the triads are reported in literature.[4, 15]

Results

The polymer products were dried overnight and used for analytical assessment. The results for enzymatic synthesis of polyesters and copolyesters illustrates the general principles of the present invention.

Nuclear Magnetic Resonance Analysis $^1$H NMR and $^{13}$C NMR (CDCl$_3$-d) data was collected on a Bruker ARX250 spectrometer. The sample concentration in CDCl$_3$ was of 6 mg/mL and the spectra were gathered at 300.0° K. For the $^1$H NMR, a relaxation delay of 2 seconds was used with 64 number of scans. Spectra were referenced to the residual CHCl$_3$ peak (at 7.3 ppm) and integrated using the UXNMR software provided by Bruker. The degree of polymerization (DP) and the number average molecular weight (Mn) values of the final polymers were assessed by end group analyses.[7] The peak area of the methylene protons neighboring the hydroxyl end group was compared to the area of methylene neighboring the oxygen in the inter-chain repeat unit. For the $^{13}$C NMR, 5 thousand scans were collected and the spectra were referenced to the $^{13}$C of CDCl$_3$-d.

Examples of subtilisin-catalyzed ring opening polyesterification of lactones and lactides are given in FIGS. 2 and 3, and FIG. 5. Polymerization of ε-caprolactone (ECL) resulted in a compound with a $^{13}$C NMR spectrum that showed peaks at ∂173.5 ppm (corresponding to the C=O in a polymeric chain) 63.98 ppm, corresponding to the εCH$_2$—O of a polymeric ester group (FIG. 2). The carbonyl and the εCH$_2$—O peak, for the control, were observed at ∂176.7 ppm and at ∂69.4 ppm respectively. In the polyester, enzymatically synthesized, a terminal group neighboring the hydroxyl end group was depicted in the $^1$H NMR spectrum at ∂3.4 ppm (see FIG. 3). Similar results were observed for the polymerization of (3S)-cis-3,6-Dimethyl-1,4-dioxane-2,5-dione (DILAC), γ-butyrolactone (GBL), and δ-valerolactone (DVL).

Gel Permeation Chromatography (GPC)

GPC analysis was performed using a Waters instrument with a refractive index detector. Gel pack column (Waters Ultrastyragel 10$^5$ Å, 10$^4$ Å, 10$^2$ Å, and 500 Å) and chloroform as eluant at a flow rate of 1 mL/min. was implemented. The calibration curve was obtained using polystyrene standards (Mn of 217600 D (daltons), 109900 D, 53100 D, 18100 g/mol, 12400 D, 4760 D, 1690 D, 503 D, correlation coefficient r$^2$=0.995412±0.006613. Examples of polymer molecular weights, conversion and degree of polymerization of the different lactones and lactides are given in FIGS. 5 to 7. Gel permeation chromatography (GPC), confirmed the presence of polymer.

Differential Scanning Calorimetry (DSC)

Thermal properties of homopolymers and copolymers synthesized by enzyme-catalyzed reactions in organic solvents were determined using a Perkin-Elmer DSC instrument (model #DSC7). Some examples of these thermal properties homopolymers and copolymers are given in FIG. 6.

In particular, ε-caprolactone (ECL) enzymatically polymerized had a crystallization temperature (Tc) of 21.5° C. and a melting temperature of 44.2° C. Glass transition temperature (Tg) was not observed for this polymer.

Polymer Morphology

The spherulite growth and morphology of the different polylactones were monitored with a Nikon Optiphot 2-POL polarizing microscope. Formation of spherulitic crystalline structures were observed for polyesters synthesized by proteases in solvents. Spherulitic radius of the polycaprolactone enzymatically polymerized was 50.8 μm, and was comparable to that found in polymers chemically synthesized.[15] The nucleation density of polycaprolactone and related polyesters synthesized by enzyme-catalyzed polymerization has increased with increasing number average molecular weight (Mn).

In addition, these polymers showed a melting point temperature (Tm) of 47.8° C. and a crystallization temperature (Tc) of 27.2° C. For these polymers, no Tg was observed. However, polydilactide was amorphous with a glass transition temperature (Tg) of −28.3° C. In addition, no Tc, Tm or spherulitic formation is detected for this polymer sample.

Gas Chromatography

Kinetics of the polymerization reaction are followed by gas chromatography. To follow monomer disappearance, aliquots of the monomer are collected from the reactions mixture at different intervals and their concentrations determined using a gas chromatography (GC, Hewlett Packard, model #5890, Series II) equipped with a capillary column (HP 1701, 30 m×0.53 mm, with a packing of thickness 1.0 μm film) and a FID detector. The sample was prepared in acetone with γ-caprolactone as the internal standard and 1 μL of the sample was injected for the GC run. The GC was set with an injection temperature of 250° C. and detector temperature of 300° C. The GC run was with a temperature gradient from 80° C. to 300° C., at the rate of 10° C. per minute. The response factor was of 1.02±0.01. Kinetic of polymerization with examples for conversion rates with different monomers, initiators and enzymes are given in FIG. 5. An example of the polymerization reaction kinetics is shown in FIG. 4. The rates conversion of ε-caprolactone (ECL) during polymerization indicated that ECL conversion was of 100% after approximately 48 hours. The figure also indicated an increase in molecular weight of the polymer during these two days. The kinetic studies also showed that the molecular weight increases slowly with conversion and this reaction may be due to chain polymerization with fast initiation and moderate chain propagation. Accordingly, considering that the enzyme activity in these first stage of the reaction is constant, it is possible to say that the rate limiting step for the reaction velocity is the ring opening.

Polymer Initiators

Polymer initiators played a key role for the ring opening polymerization using enzyme-catalyzed reactions. Different initiators were evaluated to study the rate of polymer formation, and to determine the molecular weight and dispersity of the polymer formed and degree of conversion with various lactones and lactides in the presence of different enzymes. Examples of some of the polymer parameters with different initiators are given in FIG. 5. In addition to water, hydroxylated compounds such as butanol, α-cyclodextrins, β-cyclodextrins, γ-cyclodextrins, amylose, hyaluronic acid, chitosan and starch were used as initiators for the ring opening polymerization. The molecular weight were approximately 20% lower then the corresponding polymer synthesized with water as initiator. The major drawback for these reactions is the poor yield (approximately 5%) achieved because of initiators insolubility and bulkiness.

Control of Polymer Crystallinity

Copolymerization of different lactones and lactides was used to decrease the crystallinity, and accordingly to increase the processability of copolyesters synthesized. Three monomers [ε-caprolactone (ECL), δ-valerolactone (DVL), and dilactide (DILAC)] are given as examples when used for copolymer synthesis to control their crystallinity and processability. For example, an ideal block copolymer of ECL and DVL of infinite molecular weight should only consist of VVV, EEE, VVE, and EEV triad monomer sequences, where V is δ-valerolactone (DVL), and E is ε-caprolactone (ECL). The $^{13}$C NMR resonance's can be anticipated for such copolymer.[3] By definition[14], the length of the blocks of an ideal copolymer of infinite molecular weight is:

$$\overline{L}_V = \frac{2([VVV] + [VVE])}{[VVE]} \quad (1)$$

$$\overline{L}_E = \frac{2([EE] + [EEV])}{[EEV]} \quad (2)$$

where $\overline{L}_V$ and $\overline{L}_E$ are the average lengths of the V and E blocks, respectively, (expressed in monomer units number) and [EEE], [VVV], [VVE] and [EEV] are the amounts in mole of the corresponding triads in the copolymer. Copolymers formed by ECL and DILAC (for dilactide (DILAC) the symbol D here is used for the triads), or copolymers based on DVL and DILAC, have similar equations for the assessment of block lengths. Examples of crystalline block copolymers as a function of the initial monomer feed are given in FIG. 7. The Tg was not detected for these copolymers and the melting temperatures were lower then the hompolymers at corresponding temperatures. This difference is due to the crystalline organization of the copolymer and the lower molecular weight.

Superscripted reference numerals have been used throughout the preceding text to indicate reference sources. Those numerals correspond to the following references.

1. Mayer, J. M.; Kaplan, D. L.; 2 Trends Polym. Sci., 227 (1994).
2. Klibanov, A. M.; 14 Trends Biochem. Sci., 141 (1989).
3. Hseih, H. L.; Wang, I. W.; in Ring Opening Polymerization; J. E. McGrath, Ed.; Washington D.C., 1985; 161.
4. Uyama, H.; Takeya, K.; Kobayashi, S.; 68 Bull. Chem. Soc. Jpn. 56 (1995).
5. Namekawa, S.; Uyama, H.; Kobayashi, S.; 28 Pol. J. 730 (1996).
6. Nobes, G. A. R.; Kazlauskas, R. J.; Marchessault, R. H.; 29 Macromolecules, 4829 (1996).
7. MacDonald, R. T.; Pulapura, S. K.; Svirkin, Y. Y.; Gross, R. A.; Kaplan, D. L.; Akkara, J. A.; Swift, G.; Wolk, S.; 28 Macromolecules, 73 (1995).
8. Riva, S.; Chopineau, J.; Kieboom, A. P. G.; Klibanov, A. M.; 110 Jour. Am. Chem. Soc., 584 (1988).
9. West, J. B.; Scholten, J.; Stolowich, N. J.; Hogg, J. L.; Scott, A. I.; Wong, C.; 110 Jour. Am. Chem. Soc., 3709 (1988).
10. Paradkar, V. M.; Dordick, J.; 116 Jour. Am. Chem. Soc., 5009 (1994).
11. Dordick, J. S.; 10 Trends Biotechnol., 287 (1992).
12. Rich, J. O.; Bedell, B. A.; Dordick J. S.; 45 Biotech. and Bioeng., 426 (1995).
13. Bruno, F. F.; Akkara, J. A.; Kaplan, D. L.; Gross, R.; Swift G.; Dordick, J. S.; 28 Macromolecules 8881 (1995).
14. Ammendola, P.; Zambelli, A.; Oliva, L.; Tancredi, T.; *Makromol. Chem.* 187 (1985).
15. Kricheldorf, H. R.; Berl, M.; Scharnagi, N.; 21 *Macromolecules,* 286 (1988).
16. Chen, H; Li, L.; Ou-Yang, W.; Hwang, J. C.; Wong, W.; 30 *Macromolecules,* 1718 (1997).

It will now be apparent to those skilled in the art that other embodiments, improvements, details and uses can be made consistent with the letter and spirit of the foregoing disclosure and with the scope of this patent, which is limited only by the following claims, construed in accordance with patent law, including the doctrine of equivalents.

What is claimed is:

1. A method of synthesizing polyester macromolecules by enzymatic catalysis, the method comprising the steps of:

(a) solubilizing an enzyme in a volume of hydrophobic organic solvent provided with a surfactant by formation of enzyme-surfactant ion pairs, (b) initiating an polymerization reaction by addition of a monomer to the volume of hydrophobic organic solvent containing the solubilized enzyme,
        (i) wherein the monomer reagent is selected from the group consisting of lactones having the following structure:

$$\text{(I)}\quad R\text{-}\underset{(CH_2)_n}{\underset{|}{CH}}\text{-}O\text{-}C(=O)$$

wherein
   R is hydrogen, alkyl, alkenyl, alkoxyl, cycloalkyl, cycloalkoxyl or alkylaryl group having from 0 to about 20 carbon atoms; and
   n is an integer equal to or greater than 1;
        (ii) wherein the monomer reagent is selected from the group consisting of lactides having the following structure:

$$\text{(II)}$$

wherein
   R is hydrogen, alkyl, alkenyl, alkoxyl, cycloalkyl, cycloalkoxyl or alkylaryl group having from 0 to about 20 carbon atoms (c) allowing the polymerization reaction to continue under incubation conditions, and (d) terminating the polymerization reaction by washing the macromolecule with a volume of fresh hydrophobic organic solvent to remove any unreacted monomer reagent.

2. The method, as claimed in claim 1, wherein the enzyme is a protease.

3. The method, as claimed in claim 2, wherein the enzyme is a protease from *Bacillus subtilis*.

4. The method, as claimed in claim 2, wherein the enzyme is a protease from *Bacillus species*.

5. The method, as claimed in claim 1, wherein the hydrophobic solvent is isooctane.

6. The method, as claimed in claim 1 wherein said polymer macromolecule synthesized is a homopolymer.

7. The method, as claimed in claim 6 wherein said polymer macromolecule is a homopolymer synthesized from a monomer of formula (I).

8. The method, as claimed in claim 6 wherein said polymer macromolecule is a homopolymer synthesized from a monomer of formula (II).

9. The method, as claimed in claim 1 wherein said polymer macromolecule synthesized is a copolymer.

10. The method, as claimed in claim 9 wherein said polymer macromolecule is a copolymer synthesized from two or more monomers of formula (I).

11. The method, as claimed in claim 9 wherein said polymer macromolecule is a copolymer synthesized from two or more monomers of formula (II).

12. The method, as claimed in claim 9 wherein said polymer macromolecule is a copolymer synthesized from two or more monomers of formula (I) and formula (II).

13. The method, as claimed in claim 9 wherein said polymer macromolecule is a copolymer synthesized from a monomer of formula (I) or formula (II) and a lactone or lactide monomer not of formula (I) and formula (II).

14. The method, as claimed in claim 1 wherein said polymer macromolecule synthesized is a homopolymer with well defined and predictable molecular weight and molecular weight dispersity.

15. The method, as claimed in claim 1 wherein said polymer macromolecule synthesized is a copolymer with well defined and predictable molecular weight and molecular weight dispersity.

16. The method, as claimed in claim 1 wherein said polymer macromolecule synthesized is a homopolymer with well defined crystallinity and processability.

17. The method, as claimed in claim 1 wherein said polymer macromolecule synthesized is a copolymer with well defined crystallinity and processability.

18. The method, as claimed in claim 17 wherein said polymer macromolecule synthesized is a block copolymer with well defined crystallinity and processability.

19. The method, as claimed in claim 17 wherein the composition of the crystalline block copolymer is controlled by the initial feed rate of the monomers.

20. A method of synthesizing polyester macromolecules by enzymatic catalysis, the method comprising the steps of:
   (a) solubilizing an enzyme in a volume of hydrophobic organic solvent provided with a surfactant by formation of enzyme-surfactant ion pairs,
   (b) controlling the rate and degree of polymerization by the addition of an initiator to the volume of hydrophobic organic solvent containing the solubilized enzyme,
   (c) initiating an polymerization reaction by addition of a monomer to the volume of hydrophobic organic solvent containing the solubilized enzyme,
      (i) wherein the monomer reagent is selected from the group consisting of lactones having the following structure:

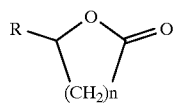

(I)

wherein
   R is hydrogen, alkyl, alkenyl, alkoxyl, cycloalkyl, cycloalkoxyl or alkylaryl group having from 0 to about 20 carbon atoms; and
   n is an integer equal to or greater than 1;
      (ii) wherein the monomer reagent is selected from the group consisting of lactides having the following structure:

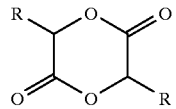

(II)

wherein
   R is hydrogen, alkyl, alkenyl, alkoxyl, cycloalkyl, cycloalkoxyl or alkylaryl group having from 0 to about 20 carbon atoms
   (d) allowing the polymerization reaction to continue under incubation conditions, and
   (e) terminating the polymerization reaction by washing the macromolecule with a volume of fresh hydrophobic organic solvent to remove any unreacted monomer reagent.

21. The method, as claimed in claim 20, wherein the initiator is a hydroxylated compound.

22. The method, as claimed in claim 21, wherein the hydroxylated initiator compound is selected from the group consisting of water, butanol, α-cyclodextrin, β-cyclodextrin, γ-cyclodextrin, amylose, hyaluronic acid and starch.

23. The method, as claimed in claim 20, wherein the enzyme is a protease.

24. The method, as claimed in claim 23, wherein the enzyme is a protease from *Bacillus subtilis*.

25. The method, as claimed in claim 23, wherein the enzyme is a protease from *Bacillus species*.

26. The method, as claimed in claim 20, wherein the hydrophobic solvent is isooctane.

27. The method, as claimed in claim 20 wherein said polymer macromolecule synthesized is a homopolymer.

28. The method, as claimed in claim 27 wherein said polymer macromolecule is a homopolymer synthesized from a monomer of formula (I).

29. The method, as claimed in claim 27 wherein said polymer macromolecule is a homopolymer synthesized from a monomer of formula (II).

30. The method, as claimed in claim 20 wherein said polymer macromolecule synthesized is a copolymer.

31. The method, as claimed in claim 30 wherein said polymer macromolecule is a copolymer synthesized from two or more monomers of formula (I).

32. The method, as claimed in claim 30 wherein said polymer macromolecule is a copolymer synthesized from two or more monomers of formula (II).

33. The method, as claimed in claim 30 wherein said polymer macromolecule is a copolymer synthesized from two or more monomers of formula (I) and formula (II).

34. The method, as claimed in claim 30 wherein said polymer macromolecule is a copolymer synthesized from a monomer of formula (I) or formula (II) and a lactone or lactide monomer not of formula (I) and formula (II).

35. The method, as claimed in claim 20 wherein said polymer macromolecule synthesized is a homopolymer with well defined and predictable molecular weight and molecular weight dispersity.

36. The method, as claimed in claim 20 wherein said polymer macromolecule synthesized is a copolymer with well defined and predictable molecular weight and molecular weight dispersity.

37. The method, as claimed in claim 20 wherein said polymer macromolecule synthesized is a homopolymer with well defined crystallinity and processability.

38. The method, as claimed in claim 20 wherein said polymer macromolecule synthesized is a copolymer with well defined crystallinity and processability.

39. The method, as claimed in claim 38 wherein said polymer macromolecule synthesized is a block copolymer with well defined crystallinity and processability.

40. The method, as claimed in claim 39 wherein the composition of the crystalline block copolymer is controlled by the initial feed rate of the monomers.

* * * * *